United States Patent
Shoeb et al.

(10) Patent No.: US 10,818,390 B1
(45) Date of Patent: Oct. 27, 2020

(54) PATTERN DISCOVERY IN CONTINUOUS GLUCOSE MONITORING DATA

(71) Applicant: Verily Life Sciences LLC, Mountain View, CA (US)

(72) Inventors: Ali Shoeb, San Rafael, CA (US); William Jacob Benhardt Biesinger, Fremont, CA (US); Joshua Burkart, Boston, MA (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 15/855,836

(22) Filed: Dec. 27, 2017

(51) Int. Cl.
| | | |
|---|---|---|
| *G16H 20/60* | (2018.01) | |
| *G16H 80/00* | (2018.01) | |
| *G09B 19/00* | (2006.01) | |
| *G09B 5/02* | (2006.01) | |
| *A61B 5/00* | (2006.01) | |
| *A61B 10/00* | (2006.01) | |
| *A61B 5/145* | (2006.01) | |
| *G06F 16/28* | (2019.01) | |

(52) U.S. Cl.
CPC ......... *G16H 20/60* (2018.01); *A61B 5/14532* (2013.01); *A61B 5/486* (2013.01); *A61B 5/4857* (2013.01); *A61B 5/4866* (2013.01); *A61B 10/0012* (2013.01); *G09B 5/02* (2013.01); *G09B 19/00* (2013.01); *G09B 19/0092* (2013.01); *G16H 80/00* (2018.01); *G06F 16/285* (2019.01)

(58) Field of Classification Search
None
See application file for complete search history.

(56) References Cited

U.S. PATENT DOCUMENTS

| 9,592,002 B2 * | 3/2017 | Schaible ............ A61B 5/14532 |
| 2009/0164251 A1 * | 6/2009 | Hayter ................ G06F 19/3456 705/3 |

(Continued)

OTHER PUBLICATIONS

Kay, Daniel, "Approaches to Display of Multiple-Point Glucose Profiles: A UK Patient's Perspective", Journal of Diabetes Science and Technology 2014; vol. 8(6), Jul. 2, 2014, pp. 1233-1238.

(Continued)

*Primary Examiner* — Eddy Saint-Vil
*Assistant Examiner* — William D Ermlick
(74) *Attorney, Agent, or Firm* — Perkins Coie LLP

(57) ABSTRACT

Introduced here are diabetes management platforms able to examine glucose measurements associated with a subject to discover patterns indicative of similar behaviors/circumstances. More specifically, a diabetes management platform can acquire multiple data series generated by a glucose monitoring device that monitors the blood glucose level of an individual over multiple time intervals. The diabetes management platform can then apply a similarity algorithm to produce a distance measure (also referred to as a "similarity measure") for each data series. For example, the diabetes management platform may, for each data series, perform dynamic time warping to produce a distance measure with respect to each of the other data series. The diabetes management platform can identify patterns indicative of similar behaviors/circumstances based on these distance measures.

18 Claims, 14 Drawing Sheets

(56) References Cited

U.S. PATENT DOCUMENTS

| | | | | |
|---|---|---|---|---|
| 2011/0046977 | A1* | 2/2011 | Goodnow | G06F 13/102 705/2 |
| 2011/0053121 | A1* | 3/2011 | Heaton | A61B 5/14532 434/127 |
| 2011/0205064 | A1* | 8/2011 | Strachan | A61B 5/14532 340/573.1 |
| 2012/0165638 | A1* | 6/2012 | Duke | A61B 5/14532 600/365 |
| 2013/0035871 | A1* | 2/2013 | Mayou | A61B 5/14532 702/26 |
| 2014/0068487 | A1* | 3/2014 | Steiger | A61B 5/7275 715/771 |
| 2014/0081103 | A1* | 3/2014 | Schaible | G16H 50/20 600/347 |
| 2014/0100435 | A1* | 4/2014 | Duke | A61B 5/7275 600/365 |
| 2014/0350369 | A1* | 11/2014 | Budiman | G06F 19/3456 600/365 |
| 2014/0365136 | A1* | 12/2014 | Mears | G16H 40/63 702/19 |
| 2015/0289823 | A1* | 10/2015 | Rack-Gomer | A61M 5/1723 600/365 |
| 2016/0042136 | A1* | 2/2016 | Groll | A61B 5/14532 345/440 |
| 2016/0098540 | A1* | 4/2016 | Zamanakos | G06T 11/206 705/2 |
| 2016/0100807 | A1* | 4/2016 | Johnson | A61B 5/14532 340/870.07 |
| 2016/0232311 | A1* | 8/2016 | Segal | G06F 19/3475 |
| 2016/0328990 | A1* | 11/2016 | Simpson | A61B 5/742 |
| 2016/0378937 | A1* | 12/2016 | Soni | G16H 50/20 705/3 |
| 2017/0053552 | A1* | 2/2017 | Zhong | A61M 5/142 |
| 2017/0224920 | A1* | 8/2017 | Finan | A61M 5/1723 |
| 2017/0251980 | A1* | 9/2017 | Duke | A61B 5/14503 |
| 2017/0329917 | A1* | 11/2017 | McRaith | A61B 5/14532 |
| 2018/0042559 | A1* | 2/2018 | Cabrera, Jr. | A61B 5/14532 |
| 2018/0150609 | A1* | 5/2018 | Kim | G06N 3/04 |
| 2018/0242891 | A1* | 8/2018 | Bernstein | G06F 19/3456 |

OTHER PUBLICATIONS

Rodbard, David, "Display of Glucose Distributions by Date, Time of Day, and Day of Week: New and Improved Methods", Journal of Diabetes Science and Technology; vol. 3, Issue 6, Nov. 2009; Nov. 6, 2009, pp. 1388-1394.

Yin, Hong et al., "A novel similarity comparison approach for dynamic ECG series", Bio-Medical Materials and Engineering 26 (2015); DOI 10.3233/BME-151406; IOS Press, 2015, pp. S1095-S1105.

* cited by examiner

|                | Data Series A | Data Series B | Data Series C | Data Series D |
|----------------|---------------|---------------|---------------|---------------|
| Data Series A  | N/A           | 0.38          | 0.04          | 0.64          |
| Data Series B  | 0.38          | N/A           | 0.27          | 0.51          |
| Data Series C  | 0.04          | 0.27          | N/A           | 0.19          |
| Data Series D  | 0.64          | 0.51          | 0.19          | N/A           |

1001
Acquire multiple data series specifying blood glucose level over multiple time intervals 1002
Apply a similarity algorithm to assess similarity between every pair of data series 1003
Create a similarity matrix from the distance measures produced by the similarity algorithm 1004
Store the similarity matrix in a database 1005
Receive input indicative of a selection of a first data series 1006
Identify a second data series that is most similar to the first data series 1007
Specify the second data series on an interface for review by an individual

FIGURE 10

PATTERN DISCOVERY IN CONTINUOUS GLUCOSE MONITORING DATA

TECHNICAL FIELD

Various embodiments concern computer programs and associated computer-implemented techniques for discovering patterns indicative of similarity between series of glucose measurements.

BACKGROUND

After ingestion of a foodstuff that contains carbohydrates, the human body breaks down the carbohydrates into glucose, which serves as a source of energy for the cells of the human body. Glucose is transported via circulation within the blood stream. Therefore, ingestion of foodstuffs will influence the concentration of glucose within the blood stream (also referred to as the "blood glucose level" or "glucose level").

According to the American Diabetes Association (ADA), a normal blood glucose level for people without diabetes is below 6.9 mmol/L (125 mg/dL). Meanwhile, the target blood glucose range for people with diabetes is 5.0-7.2 mmol/L (90-130 mg/dL) before meals and less than 10 mmol/L (180 mg/dL) after meals. However, some people with diabetes struggle to consistently stay within the recommended range.

BRIEF DESCRIPTION OF THE DRAWINGS

Various features and characteristics of the technology will become more apparent to those skilled in the art from a study of the Detailed Description in conjunction with the drawings. Embodiments of the technology are illustrated by way of example and not limitation in the drawings, in which like references may indicate similar elements.

FIG. 4A depicts an example of a similarity matrix including distance measures that have been normalized to a 0-1 range.

FIG. 10 depicts a flow diagram of a process for identifying similar data series in response to a selection of a specified data series.

Figure 1:
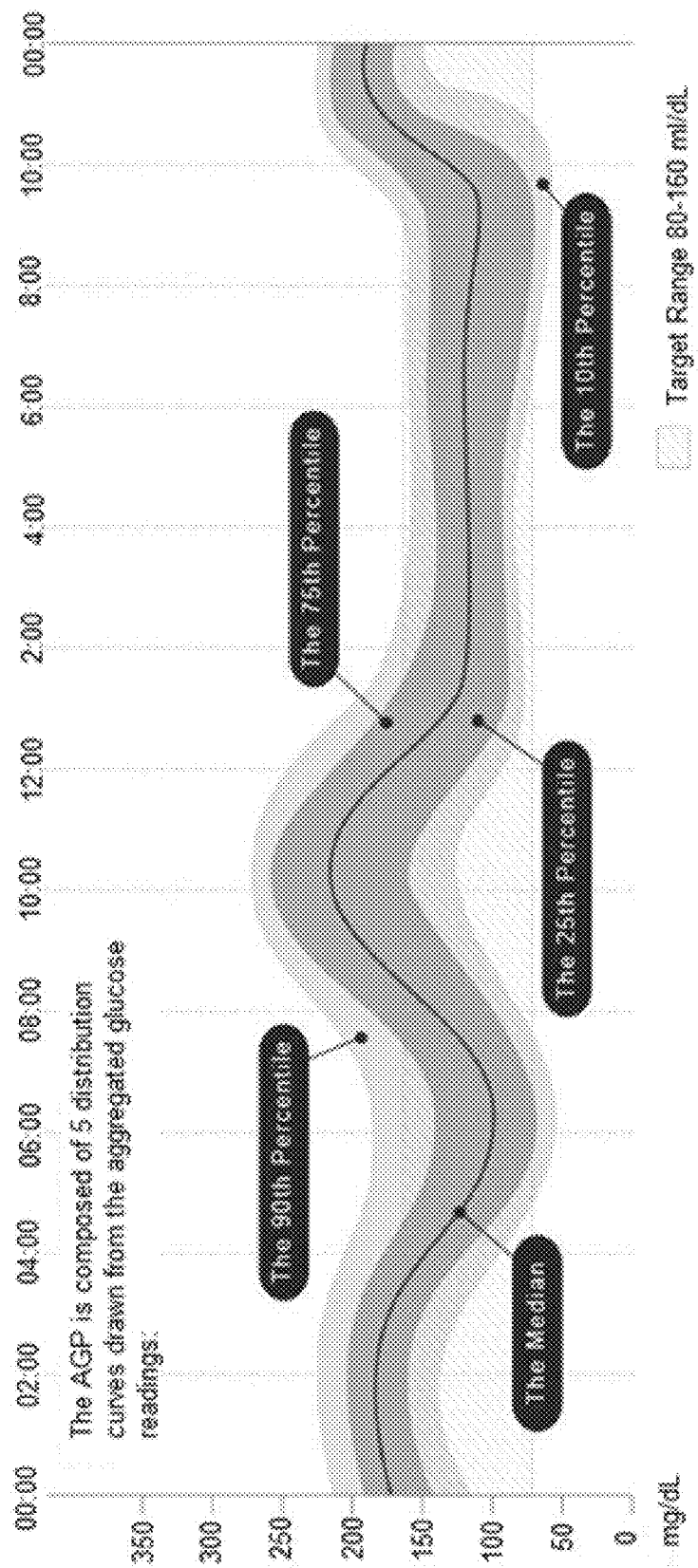
FIG. 1 depicts an ambulatory glucose profile (AGP), which is a visualization of blood glucose level over time.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Diabetes mellitus (commonly referred to as "diabetes") is a group of metabolic disorders in which the affected individuals experience high blood glucose levels over a prolonged period. If left untreated, diabetes can cause many complications. For example, long-term complications can include cardiovascular disease, stroke, chronic kidney disease, foot ulcers, and eye damage.

Individuals with diabetes can benefit from education about treatment, good nutrition to achieve a normal body weight, and exercise. However, some of those individuals may find it difficult to implement lifestyle changes that promote healthier blood glucose levels. Moreover, some of these individuals may find it difficult to understand blood glucose level measurements, which represent a technical signal indicative of the diabetes disease state.

Continuous glucose monitoring represents a promising new way for individuals to gain insights into the diabetes disease state. For example, an individual may be able to observe how consumption of a certain foodstuff or performance of a certain activity affects blood glucose level. Historically, an individual with diabetes would take several blood glucose measurements throughout the day in an ad hoc manner using a blood glucose meter (BGM). A continuous glucose monitor (CGM), meanwhile, can continually monitor the blood glucose level throughout the day. For example, a CGM may automatically take blood glucose measurements every five minutes, ten minutes, etc.

Visualizations can be helpful in conveying the importance of blood glucose level variations detected by these glucose monitoring devices. One example is the ambulatory glucose profile (AGP) as shown in FIG. 1. The AGP offers a visualization of blood glucose level that is readily understandable. Similar to an electrocardiogram in cardiology, the AGP can collapse physiological data collected over several days or weeks into a single 24-hour period, thereby creating a model day. The AGP can reveal underlying patterns in blood glucose variability to a greater extent than static measurements.

With vastly more data, however, comes the need for better visualizations. Simply stacking data from different time intervals can be difficult to qualitatively interpret, even for professional diabetes educators and health coaches responsible for monitoring the glycemic health of individuals with diabetes (also referred to as "subjects" or "patients"). In some embodiments each time interval is 24 hours in length to match a circadian cycle, so analysis of multiple time intervals may be of consecutive days. In other embodiments each time interval is between 3 and 12 hours in length to match a feeding cycle, so analysis of multiple time intervals may be of a similar time period across multiple days (e.g., mornings, afternoons, or evenings). Thus, each time interval could be associated with, and correspond to, a natural rhythm or cycle. Examples of natural rhythms/cycles include a circadian cycle, a menstrual cycle, a feeding cycle, an elimination cycle, etc.

Introduced here, therefore, are computer programs and associated computer-implemented techniques for examining/visualizing glucose measurements. More specifically, a diabetes management platform can acquire multiple data series generated by a glucose monitoring device that monitors the blood glucose level of an individual over multiple time intervals. The glucose monitoring device may be a CGM or a BGM. Each data series, therefore, may include discrete digitally represented values in a temporal order that are indicative of time-varying glucose concentrations sampled periodically.

The diabetes management platform can then apply a similarity algorithm to produce a distance measure (also referred to as a "similarity measure") for each data series. For example, the diabetes management platform may, for each data series, perform dynamic time warping to produce a distance measure with respect to each of the other data series. Thus, the diabetes management platform may dynamically find an optimal alignment between two given time-dependent data series. The distance measure is indicative of the similarity between a pair of data series. Similar data series will generally be associated with low distance measures, while dissimilar data series will generally be associated with high distance measures.

In some embodiments, the diabetes management platform produces a similarity matrix from the distance measures associated with the multiple data series. The similarity matrix can enable the diabetes management platform to readily determine the similarity between any pair of data series.

The diabetes management platform may sort the multiple data series into clusters based on the distance measures included in the similarity matrix. More specifically, the diabetes management platform may apply a spectral clustering algorithm to discover data series covering similar real-world behaviors. For example, the spectral clustering algorithm may identify the time intervals corresponding to the data series that are least/most similar to a target data series indicative of a healthy glycemic state. The target data series may correspond to the glycemic range considered to be normal by the American Diabetes Association (ADA). Thus, the diabetes management platform may be able to easily identify "good" time intervals in which the blood glucose level is within a healthy range and/or "bad" time intervals in which the blood glucose level is not within the healthy range.

Embodiments may be described with reference to particular computer programs, system configurations, networks, etc. However, those skilled in the art will recognize that these features are equally applicable to other computer program types, system configurations, network types, etc. Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program an electronic device to perform a process for examining data series including blood glucose measurements, discovering patterns indicative of similarity between the data series, producing visualizations of the data series, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

The term "based on" is also to be construed in an inclusive sense rather than an exclusive or exhaustive sense. Thus, unless otherwise noted, the term "based on" is intended to mean "based at least in part on."

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For examples, steps could be added to, or removed from, the processes described here. Similarly, steps could be replaced or reordered. Thus, descriptions of any processes are intended to be open-ended.

Technology Overview

Figure 2:
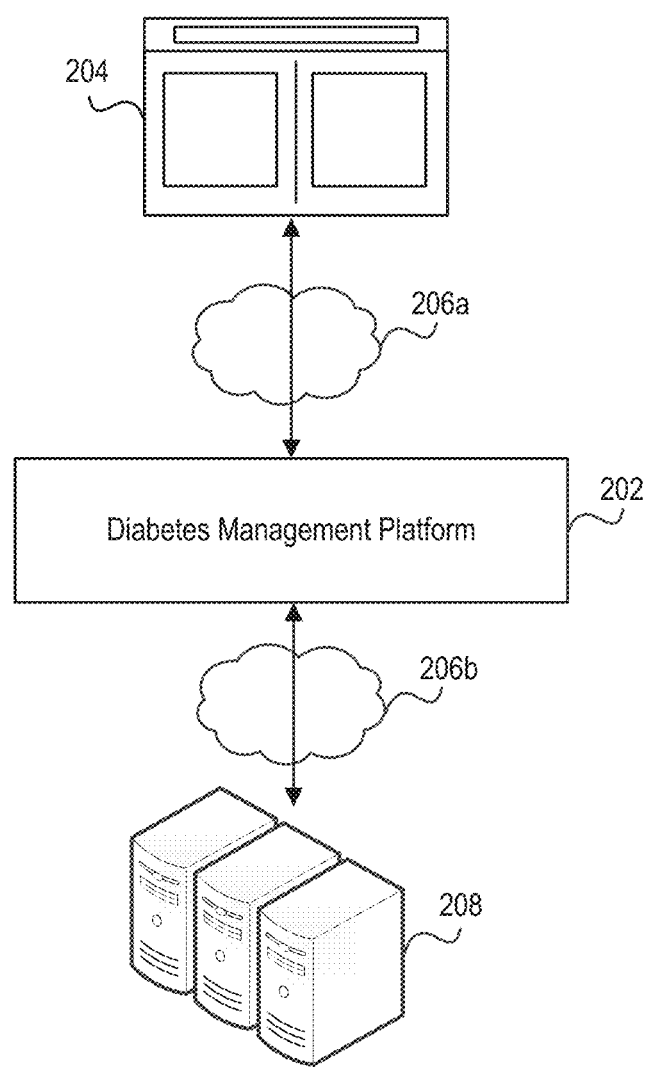
FIG. 2 illustrates a network environment that includes a diabetes management platform.

FIG. 2 illustrates a network environment 200 that includes a diabetes management platform 202. Individuals can interface with the diabetes management platform 202 via an interface 204. The diabetes management platform 202 may be responsible for parsing physiological data pertaining to an individual to discover variations in blood glucose level, detect patterns indicative of similarity between different segments of data, generate recommendations for guiding the individual toward a healthier glycemic state, etc. The diabetes management platform 202 may also be responsible for creating interfaces through which the individual can view physiological data, manage preferences, etc.

Physiological data could specify the blood glucose level of the individual accessing the interface 204 or some other person. For example, in some embodiments the interface 204 enables a person with diabetes to view their own physiological data, while in other embodiments the interface 204 enables an individual to view physiological data associated with some other person. The individual may be a health coach responsible for monitoring the glycemic health of the other person. Examples of health coaches include medical professionals (e.g., a physician or nurse), diabetic health counselors, family members of the other person, etc. Some interfaces are configured to facilitate interactions between subjects and health coaches, while other interfaces are configured to serve as informative dashboards for subjects.

As noted above, the diabetes management platform 202 may reside in a network environment 200. Thus, the diabetes management platform 202 may be connected to one or more networks 206a-b. The network(s) 206a-b can include personal area networks (PANs), local area networks (LANs), wide area networks (WANs), metropolitan area networks (MANs), cellular networks, the Internet, etc. Additionally or alternatively, the diabetes management platform 202 can be communicatively coupled with computing device(s) over a short-range communication protocol, such as Bluetooth® or Near Field Communication (NFC).

The interface 204 is preferably accessible via some combination of a web browser, desktop application, mobile application, or over-the-top (OTT) application. Accordingly, the interface 204 may be viewed on a personal computer, tablet computer, personal digital assistant (PDA), mobile phone, game console, music player, wearable electronic device (e.g., a watch or fitness accessory), network-connected ("smart") electronic device, (e.g., a television or home assistant device), virtual/augmented reality system (e.g., a head-mounted display), or some other electronic device.

Some embodiments of the diabetes management platform 202 are hosted locally. That is, the diabetes management platform 202 may reside on the computing device used to access the interface 204. For example, the diabetes management platform 202 may be embodied as a mobile application executing on a mobile phone. Other embodiments of the diabetes management platform 202 are executed by a cloud computing service operated by Amazon Web Services® (AWS), Google Cloud Platform™, Microsoft Azure®, or a similar technology. In such embodiments, the diabetes management platform 202 may reside on a host computer server that is communicatively coupled to one or more content computer servers 208. The content computer server(s) 208 can include different types of data, user information (e.g., profiles, credentials, and health-related information such as age, diabetes classification, etc.), and other assets. Such information could also be stored on the host computer server.

Certain embodiments are described in the context of network-accessible interfaces. However, those skilled in the art will recognize that the interfaces need not necessarily be accessible via a network. For example, a computing device may be configured to execute a self-contained computer program that does not require network access. Instead, the self-contained computer program may cause necessary assets (e.g., physiological data, healthcare regimen data, and processing operations) to be downloaded at a single point in time or on a periodic basis (e.g., weekly, daily, or hourly).

Figure 3:
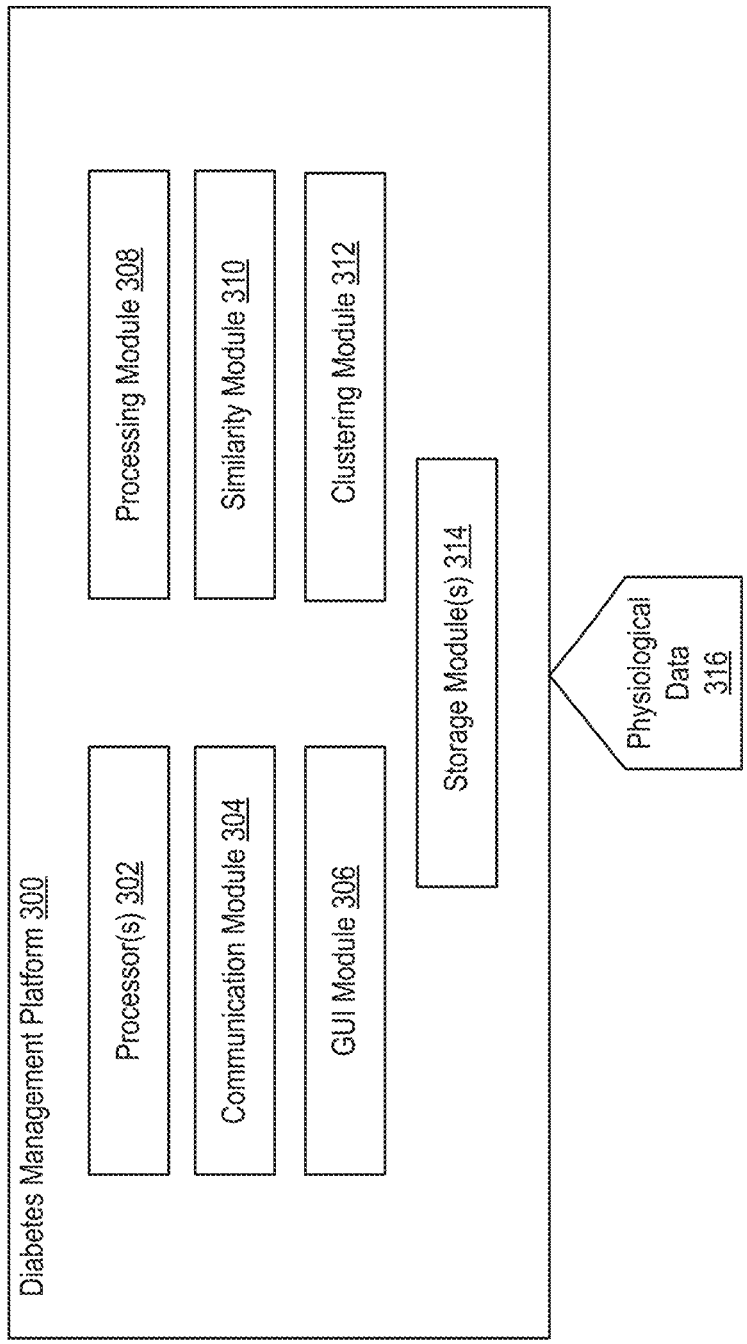
FIG. 3 depicts the high-level architecture of a diabetes management platform able to cluster series of physiological data to enable the discovery of patterns indicative of similarity between certain data series, as well as the production of better visualizations of blood glucose level.

FIG. 3 depicts the high-level architecture of a diabetes management platform 300 able to cluster series of physiological data to enable the discovery of patterns indicative of similarity between certain data series, as well as the production of better visualizations of blood glucose level. As shown in FIG. 2, an individual can interface with the diabetes management platform 300 via an interface. The individual may be a person with diabetes or another person with an interest in the blood glucose level of the person with diabetes.

The diabetes management platform 300 can include one or more processors 302, a communication module 304, a graphical user interface (GUI) module 306, a processing module 308, a similarity module 310, a clustering module 312, and one or more storage modules 314. In some embodiments a single storage module includes multiple computer programs for performing different operations (e.g., format conversion and statistical analysis), while in other embodiments each computer program is hosted within a separate storage module. Embodiments of the diabetes management platform 300 may include some or all of these components, as well as other components not shown here.

The processor(s) 302 can execute modules from instructions stored in the storage module(s) 314, which can be any device or mechanism capable of storing information. For example, the processor(s) 302 may execute the GUI module 306, processing module 308, similarity module 310, and clustering module 312.

The communication module 304 can manage communications between various components of the diabetes management platform 300. The communication module 304 can also manage communications between the computing device on which the diabetes management platform 300 resides and another computing device.

For example, the diabetes management platform 300 may reside on a mobile phone in the form of a mobile application. In such embodiments, the communication module 304 can facilitate communication with a network-accessible computer server responsible for supporting the mobile application. The communication module 304 may facilitate communication with various data sources through the use of application programming interfaces (APIs), bulk data interfaces, etc.

As another example, the diabetes management platform 300 may reside on a server system that includes one or more network-accessible computer servers. In such embodiments, the communication module 304 can communicate with a computer program executing on the computing device associated with the individual. Those skilled in the art will recognize that the components of the diabetes management platform 300 can be distributed between the server system and the computing device associated with the individual in various manners. For example, some data (e.g., physiological data) may reside on the computing device of the individual, while other data (e.g., processing operations and feedback for causing the individual to progress toward a healthier glycemic state) may reside on the server system.

The GUI module 306 can generate the interface(s) through which an individual can interact with the diabetes management platform 300. For example, an interface may include a graphical representation of blood glucose level over time. As another example, an interface may include an overlay visualization of multiple data series corresponding to different time intervals. These interfaces may also present feedback/suggestions for improving the health state (e.g., by performing certain activities, refraining from consuming certain foodstuffs, etc.).

The processing module 308 can apply one or more operations to physiological data 316 acquired by the diabetes management platform 300. Physiological data 316 specifying the blood glucose level of an individual could be generated by a glucose monitoring device. Examples of glucose monitoring devices include continuous glucose monitors and blood glucose meters.

A glucose monitoring device may be configured to continuously or periodically transmit physiological data 316 to the diabetes management platform 300. In some embodiments, the glucose monitoring device continually uploads physiological data 316 to the diabetes management platform 300 so long as the glucose monitoring device remains communicatively coupled to the computing device on which the diabetes management platform 300 resides (e.g., via a Bluetooth® communication channel). In other embodiments, the glucose monitoring device periodically uploads physiological data 316 to the diabetes management platform 300 on a periodic basis (e.g., hourly, daily, or weekly). In such embodiments, the physiological data 316 may include multiple data sets (e.g., a first data set for a first time interval, a second data set for a second time interval, etc.).

The processing module 308 can process the physiological data 316 into a format suitable for the other modules (e.g., the similarity module 310, clustering module 312, or storage module(s) 314). The processing module 308 can also parse the physiological data 316 to identify certain characteristic(s) of the blood glucose level. For example, the processing module 308 may calculate metrics that are critical in guiding diabetes treatment in a personalized manner. These metrics can include time-in-range, glycemic variability, glycemic exposure, hypoglycemia range, hyperglycemia range, etc.

The similarity module 310 can apply a similarity algorithm to multiple series of physiological data to produce a distance measure (also referred to as a "similarity measure") for each data series. For example, the similarity module 310 may, for each data series, perform dynamic time warping to produce a distance measure with respect to each of the other data series. Each distance measure is indicative of the similarity between the corresponding pair of data series. Similar data series will generally be associated with low distance measures, while dissimilar data series will generally be associated with high distance measures. For example, a pair of identical data series may produce a distance measure of zero. Thus, as the pair of data series become increasing dissimilar, the value of the distance measure may increase.

In some embodiments, the similarity module 310 produces a similarity matrix from the distance measures associated with the multiple series of physiological data. FIG. 4A depicts an example of a similarity matrix, which enables the similarity module 310 to determine which data series are most similar (here, data series A and data series C) and which data series are least similar (here, data series A and data series D). The distance measures shown in FIG. 4A have been normalized to a 0-1 range. However, those skilled in the art will recognize that the distance measures could vary within any range of values. The similarity matrix can enable the similarity module 310 to readily determine the similarity between any pair of data series.

The clustering module 312 can sort the multiple series of physiological data into clusters based on the distance measures produced by the similarity module 310. The clustering module 312 can apply different algorithm(s) for clustering analysis as are known in the art, such as the hierarchical clustering technique and the k-means clustering technique.

Generally, clustering analysis refers to group objects (here, data series) in such a way that objects in the same group (referred to as a "cluster") are more similar to each other than to those objects in other clusters. In some embodiments, the clustering module 312 forms clusters based on natural segments in the data series. For example, the clustering module 312 may discover that a first subset of data series that are only similar to one another, a second subset of data series that are only similar to one another, etc. In other embodiments, the clustering module 312 applies a well-defined framework for distributing data series amongst a specified number of clusters. For example, the clustering module 312 may automatically form a specified number of clusters based on pre-defined ranges of distance values (e.g., every 0.1, 0.25, or 0.33 for distance measures normalized to a 0-1 range).

More specifically, the clustering module 312 may apply a spectral clustering algorithm to discover data series covering similar real-world behaviors. For example, the spectral clustering algorithm may identify the time intervals corresponding to the data series that are least/most similar to a target data series corresponding to a healthy glycemic state. The target data series may be a baseline representing the blood glucose levels and the glycemic responses considered to be normal by the American Diabetes Association (ADA). The target data series may correspond to the actual blood glucose measurements of an individual without diabetes. Alternatively, the target data series may be fabricated based on the glycemic range known to be indicative of a healthy glycemic state.

The spectral clustering algorithm may detect, based on the distance measures, whether the multiple series of physiological data form any clusters. Clusters are generally indicative of similar behavior(s). Thus, if the clustering module 312 determines that multiple data series are similar to one another, then the clustering module 312 may examine the multiple data series to determine whether the multiple data series share a characteristic. In some embodiments the shared characteristic is reflected in the multiple data series, while in other embodiments the shared characteristic is derivable from the multiple data series or metadata provided with the multiple data series. The shared characteristic could be a time of day, a day of the week, an activity, a foodstuff, etc. For example, the clustering module 312 may determine that the blood glucose level of the individual is consistently at an unhealthy level during the mornings. As another example, the clustering module 312 may determine that the blood glucose level of the individual is consistently at an unhealthy level during the weekends. Thus, the clustering module 312 may be able to easily identify "good" time intervals in which the blood glucose level is within a healthy range and/or "bad" time intervals in which the blood glucose level is not within the healthy range.

Figure 4B:
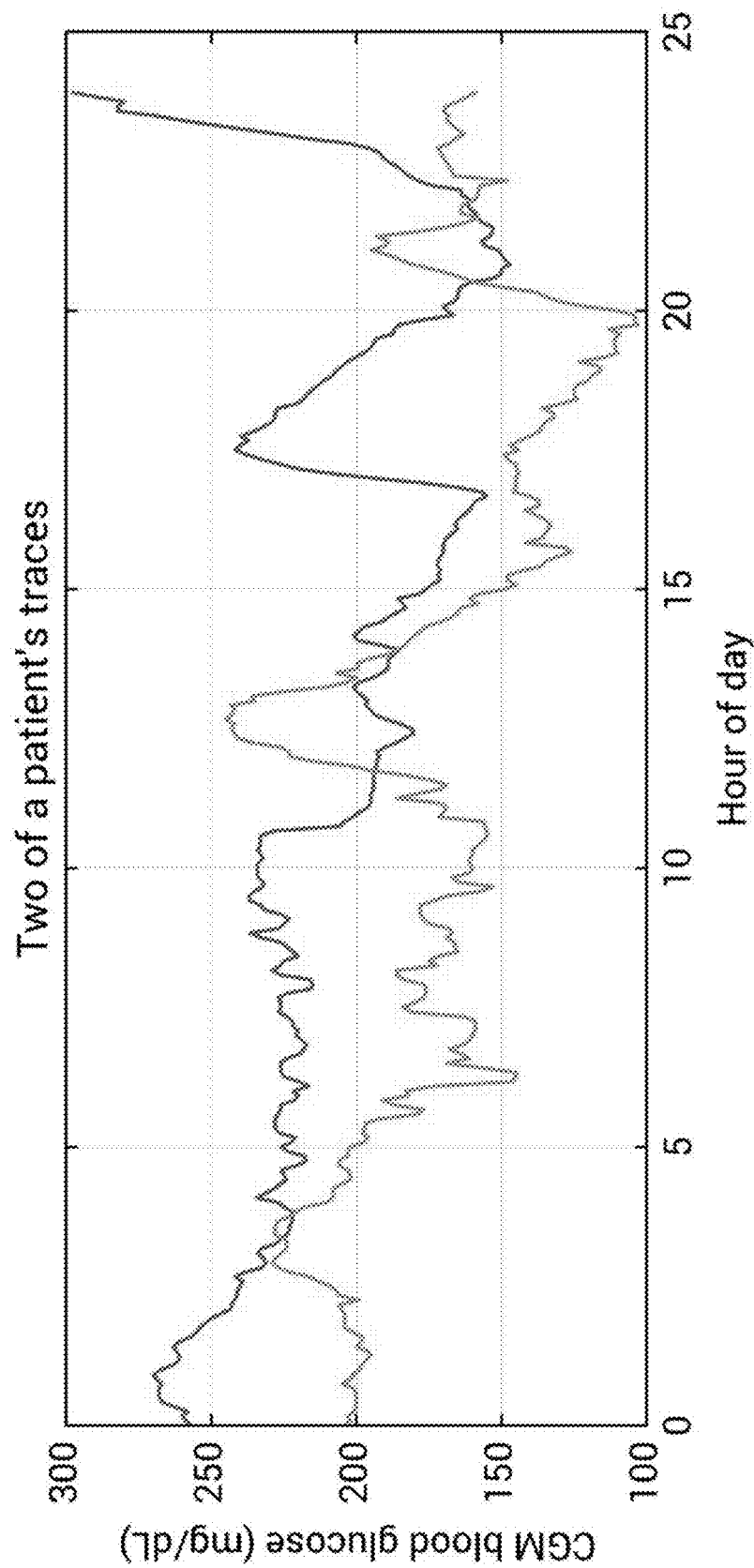
FIG. 4B depicts two separate glucose traces corresponding to consecutive days.

FIG. 4B depicts two separate glucose traces corresponding to consecutive days. If the data series corresponding to the glucose traces were not warped in the time dimension, then a diabetes management platform would discover that the data series are incredibly dissimilar on an entry-by-entry basis.

Figure 4C:
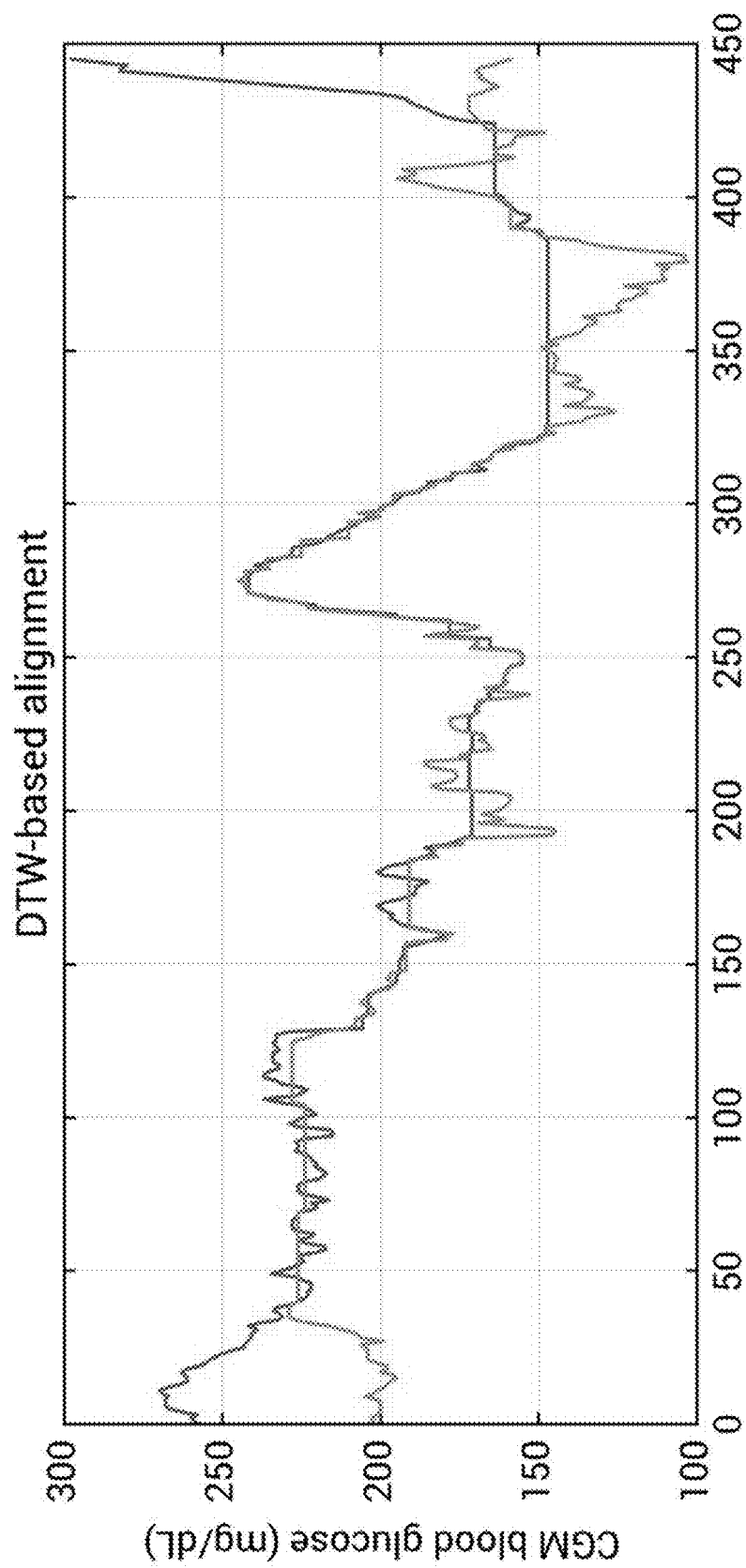
FIG. 4C depicts the two separate glucose traces following dynamic time warping.

Thus, the diabetes management platform may perform dynamic time warping to ensure that the data series are non-linearly warped in the time dimension. FIG. 4C depicts the two separate glucose traces following dynamic time warping. Such action will produce distance measures that are independent of non-linear variations in the time dimension. Thus, the data series can be non-linearly warped to avoid being categorized as dissimilar simply because the subject consumed a meal at 12 PM on one day and 4 PM the next day.

Figure 5:
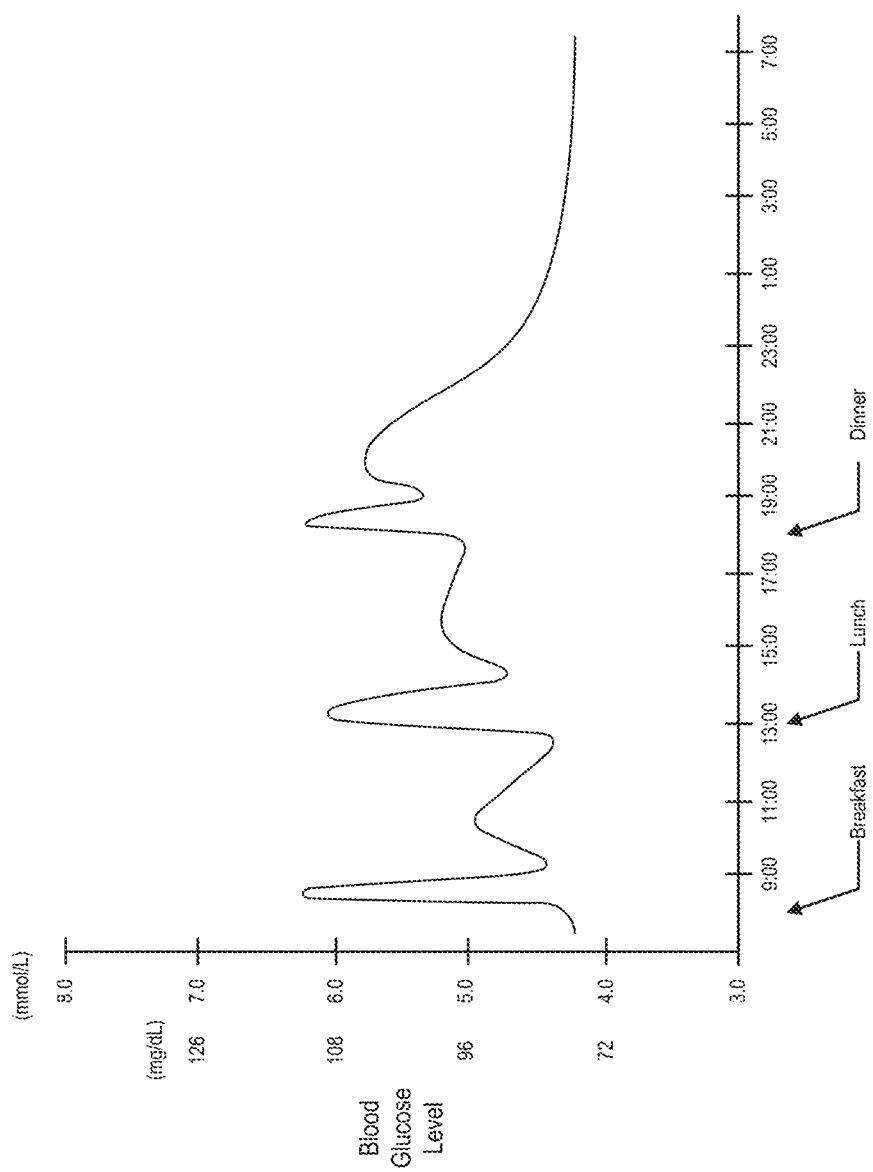
FIG. 5 illustrates how the blood glucose level can vary throughout the day.

FIG. 5 illustrates how the blood glucose level can vary throughout the day. As shown here, the blood glucose level will increase following the ingestion of a foodstuff, and then steadily decrease thereafter. Foodstuffs having a high glycemic index are more rapidly digested, and thus cause substantial fluctuations in the blood glucose level over a short period of time.

According to the ADA, a normal blood glucose level for people without diabetes is below 6.9 mmol/L (125 mg/dL). Meanwhile, the target blood glucose range for people with diabetes is 5.0-7.2 mmol/L (90-130 mg/dL) before meals and less than 10 mmol/L (180 mg/dL) after meals. However, some people with diabetes struggle to consistently stay within the recommended range. For example, individuals with blood glucose levels that are consistently above 7.0 mmol/L (126 mg/dL) are generally considered to have hyperglycemia, while individuals with blood glucose levels that are consistently below 4.0 mmol/L (70 mg/dL) are generally considered to have hypoglycemia.

Visualizations can be helpful in conveying the importance of blood glucose level variations. One example is the ambulatory glucose profile (AGP) as shown in FIG. 1. Another example is a line chart of continuous glucose monitoring data over time as shown in FIG. 5.

Figure 6:
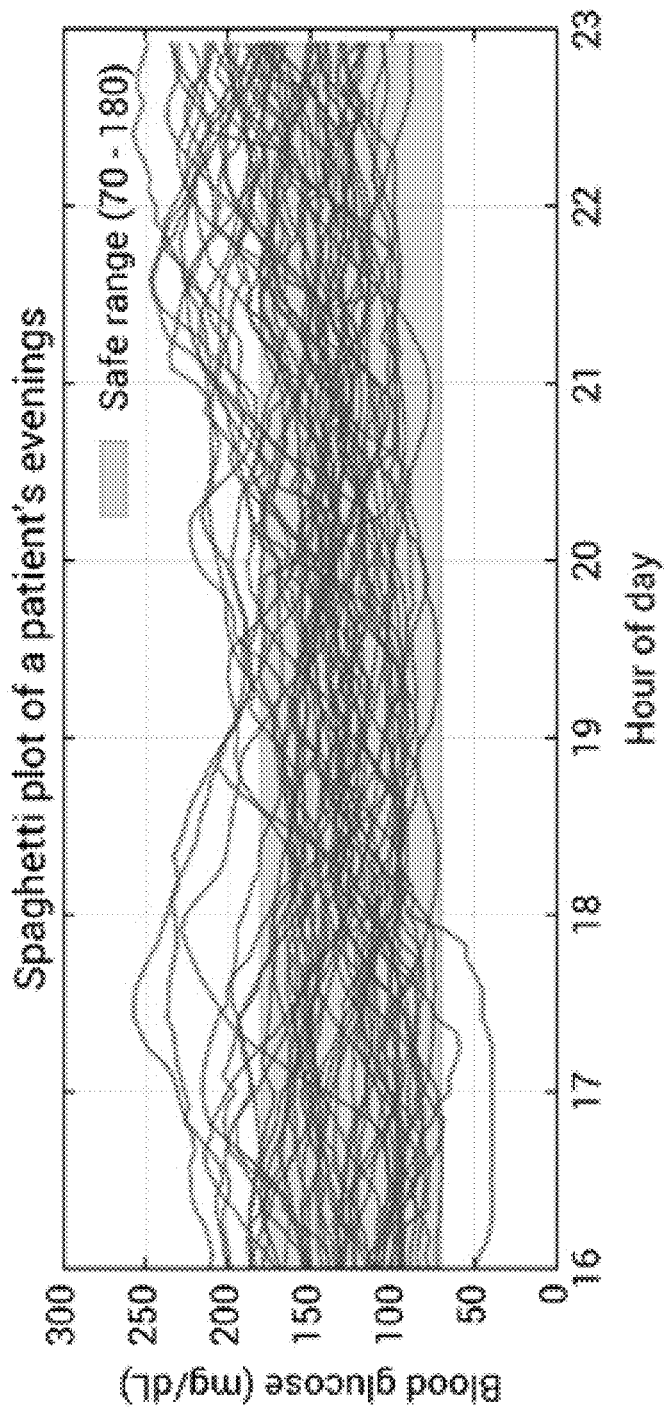
FIG. 6 depicts an example of a spaghetti plot that includes a different line for each evening over the course of several weeks.

With vastly more data, however, comes the need for better visualizations. Simply stacking data from different time intervals can be difficult to qualitatively interpret, even for professional diabetes educators and health coaches responsible for monitoring the glycemic health of individuals with diabetes. FIG. 6 depicts an example of a spaghetti plot that includes a different line for each evening over the course of several weeks. While such a spaghetti plot may illustrate general trends (e.g., blood glucose level is most consistent from 7-8 PM), the spaghetti plot cannot be used to generate personalized feedback that is useful in guiding the subject toward a healthier glycemic state.

Figure 7A:
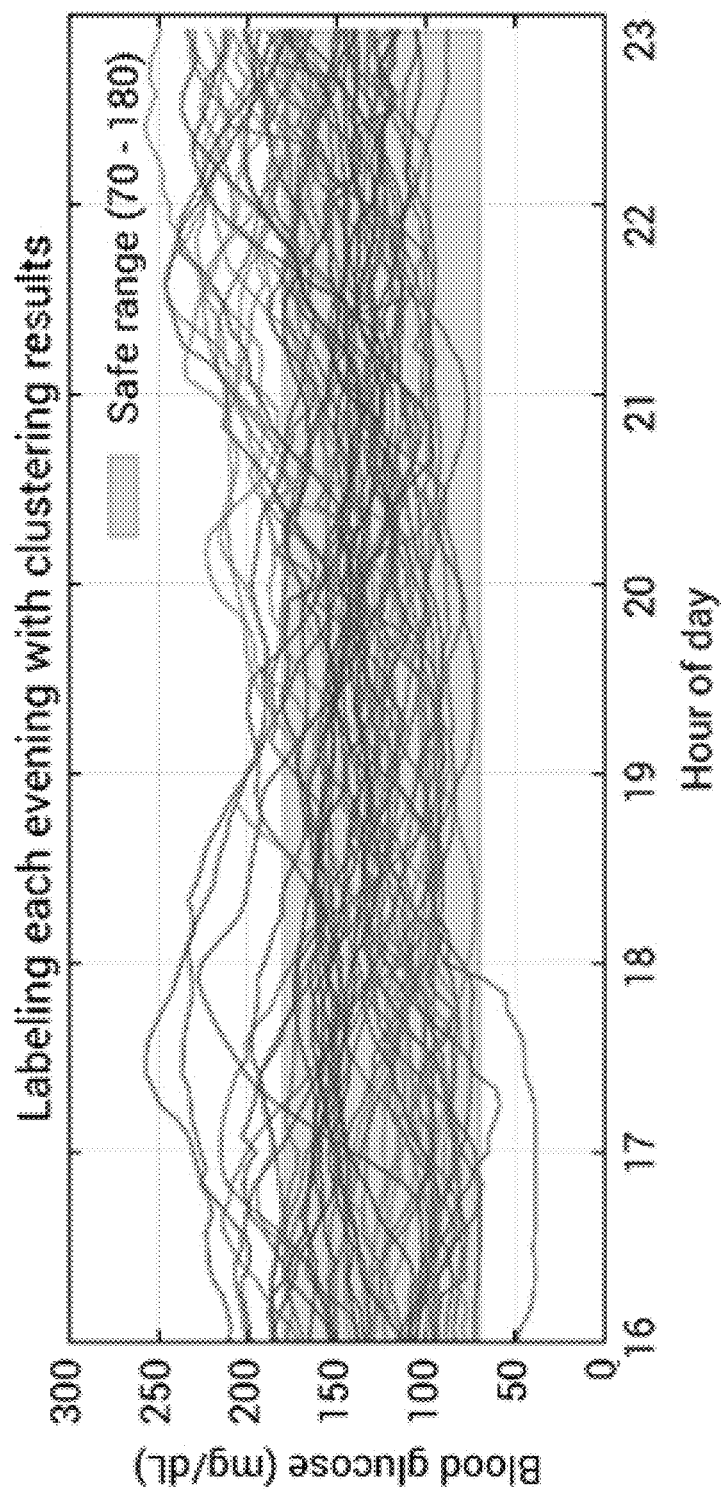
FIG. 7A depicts an example of a color-coded spaghetti plot that includes a different line for each evening over the course of several weeks.
Figure 7B:
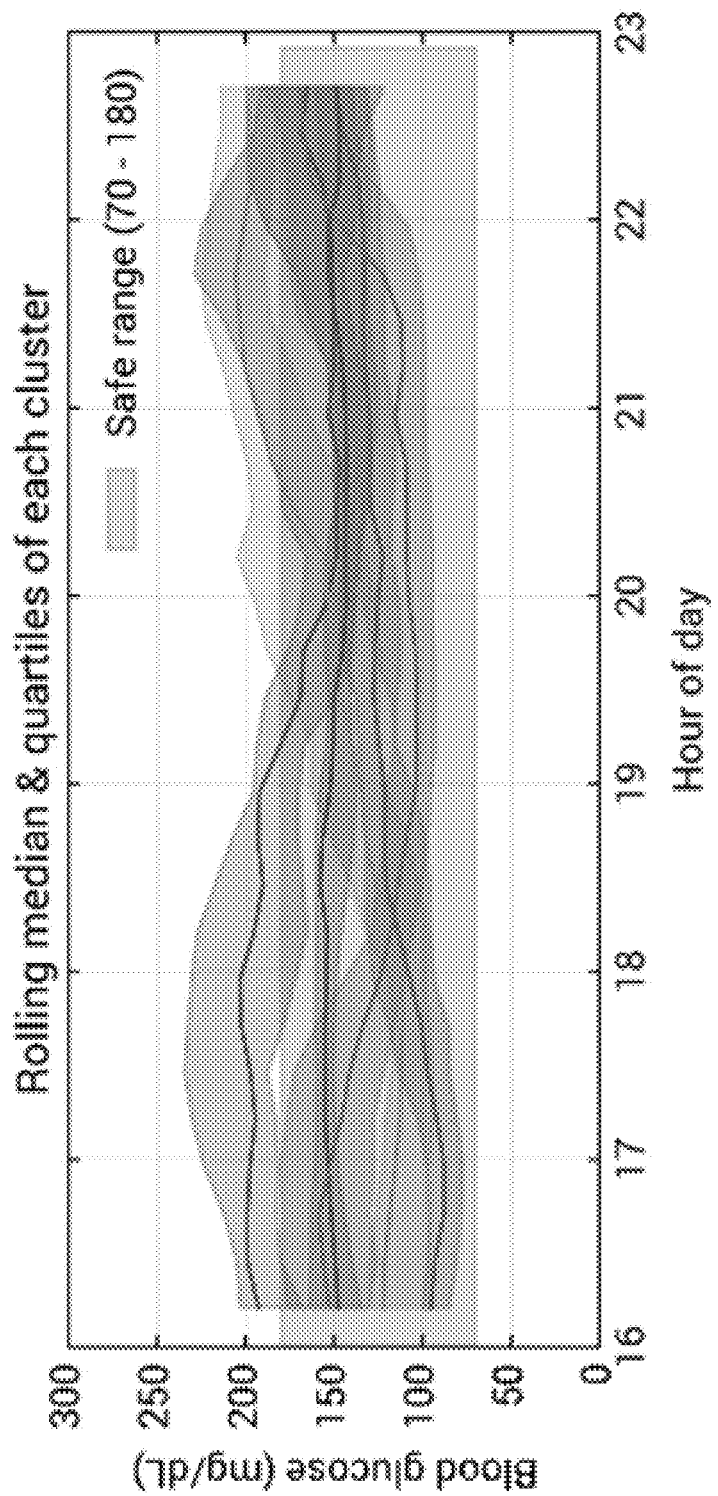
FIG. 7B depicts the rolling median and quartiles corresponding to each cluster shown in FIG. 7A.

Introduced here, therefore, are computer programs and associated computer-implemented techniques for examining visualizing glucose measurements. More specifically, a diabetes management platform can intelligently visualize different clusters of glucose measurements so that commonalities can be more easily detected. Similar to FIG. 6, FIG. 7A depicts an example of a spaghetti plot that includes a different line for each evening over the course of several weeks. Here, however, each cluster of data series is associated with a different color. This allows an individual reviewing the chart to identify which data series are associated with consistently high/low blood glucose levels, whether those data series share any characteristics in common, etc. FIG. 7B, meanwhile, depicts the rolling median and quartiles corresponding to each cluster.

The computer programs and associated computer-implemented techniques introduced here enable several benefits, including:

An ability to show data series corresponding to a certain time period (e.g., a day, week, or month);
An ability to indicate which time interval(s) belong to which cluster(s);
An ability to detect time intervals (referred to as "outliers") that were significantly different than other time intervals; and
An ability to discover relevant patterns based on importance (e.g., variation in blood glucose level), frequency (e.g., number of data series included in a specified cluster), etc.

Figure 8:
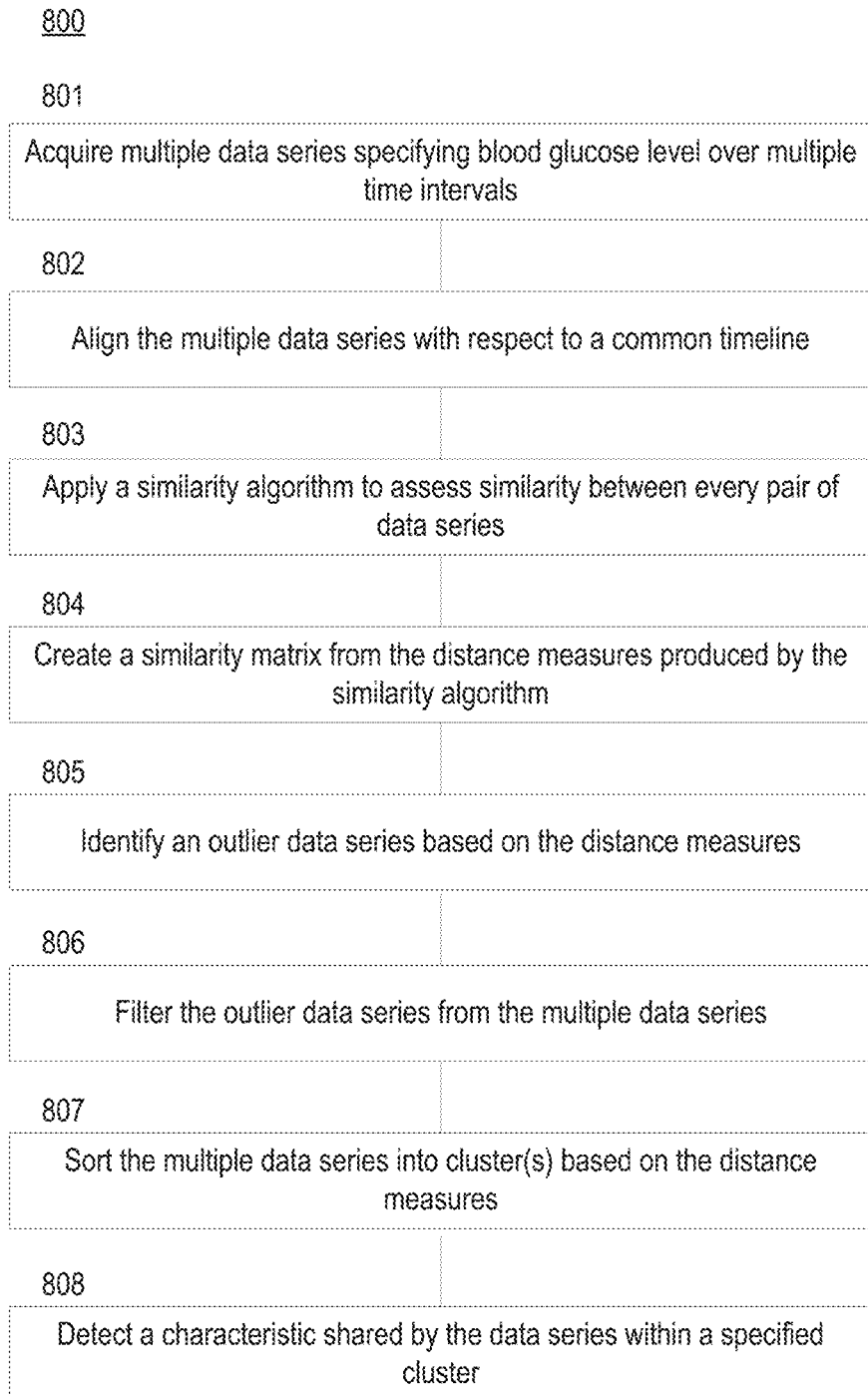
FIG. 8 depicts a flow diagram of a process for discovering characteristic(s) shared between certain series of physiological data.

FIG. 8 depicts a flow diagram of a process 800 for discovering characteristic(s) shared between certain series of physiological data. These characteristic(s) may be used to guide an individual toward a healthier glycemic state. For example, a diabetes management platform may flag negative characteristic(s) associated with unhealthy blood glucose measurements. As another example, the diabetes management platform may flag positive characteristic(s) associated with healthy blood glucose measurements.

Initially, the diabetes management platform acquires multiple series of physiological data specifying the blood glucose level of an individual over multiple time intervals (step 801). Each data series of the multiple data series may correspond to a different time interval of the multiple time intervals. In some embodiments, the diabetes management platform aligns the multiple data series with respect to a common timeline (step 802). Thus, the diabetes management platform may stack data series from similar time intervals. In some embodiments each time interval corresponds to a different day (i.e., a 24-hour segment), while in other embodiments each time interval corresponds to a multi-hour segment (e.g., a 4-hour segment, 8-hour segment, or 12-hour segment). Thus, the diabetes management platform could examine data series pertaining to mornings, afternoons, or evenings over the course of a week, month, etc.

The diabetes management platform can then apply a similarity algorithm to assess similarity for every possible pair of the multiple data series (step 803). For example, the diabetes management platform may perform, for each data series of the multiple data series, dynamic time warping to produce a distance measure for each of the other data series. Each distance measure is indicative of the similarity between the corresponding pair of data series. Dynamic time warping may require that the pair of data series being examined are non-linearly warped in the time dimension. Such action will produce distance measures that are independent of non-linear variations in the time dimension.

The diabetes management platform may also create a similarity matrix from the distance measures associated with each data series of the multiple data series (step 804). In some embodiments, the diabetes management platform identifies at least one outlier data series based on the distance measures included in the similarity matrix (step 805). A data series may be identified as an outlier if each distance measure associated with the data series exceeds a specified amount (i.e., the data series is not considered statistically similar to any other data series). In such embodiments, the diabetes management platform may filter the at least one outlier data series from the multiple data series (step 806), which may ensure the at least one outlier data series is not considered by the diabetes management platform when forming clusters. Filtering can be governed by one or more statistical rules. These statistical rule(s) may define the outlier threshold that governs which data series should be filtered out. For example, a statistical rule may cause a data series to be identified as an outlier data series if each distance measure associated with the data series exceeds a specified amount (e.g., 0.5 or 0.7 for distance measures normalized to a 0-1 range). As another example, a statistical rule may cause a data series to be identified as an outlier data series if no other data series correspond to a similar timeframe (e.g., the data series is the only one covering 12 AM to 6 AM).

The diabetes management platform can then sort the multiple data series into one or more clusters based on the distance measures (step 807). More specifically, the diabetes management platform may apply a clustering algorithm to the similarity matrix to form the cluster(s). The clustering algorithm may automatically determine how many clusters should exist (e.g., based on the natural grouping of distance measures), which data series should be assigned to which clusters, how many data series are in each cluster, etc. Some of these features could also be manually specified by an individual. For example, an individual may specify the multiple data series should be distributed amongst a certain number of clusters. As another example, the individual may specify the range of distance measure values included in each cluster, thereby affecting how alike a pair of data must be to be considered similar to one another.

After identifying a specified cluster that includes one or more data series, the diabetes management platform can detect a characteristic shared by the data series (step 808). The cluster may be automatically specified by the diabetes management platform or manually specified by an individual (e.g., a health coach) reviewing the cluster(s). Thus, the diabetes management platform may receive input indicative of a selection of the specified cluster. The shared characteristic could be a time of day, a day of the week, an activity, a foodstuff, etc.

Thus, if the diabetes management platform examines the cluster that includes the data series that are least similar to a target data series corresponding to a healthy glycemic state, then the diabetes management platform can discover characteristic(s) of "bad" time intervals in which the blood glucose level is not within the healthy range. For example, the diabetes management platform may determine that the blood glucose level of the individual is consistently at an unhealthy level on Sundays, following the performance of a certain activity (e.g., attending a party), following the consumption of a certain foodstuff, etc. As another example, the diabetes management platform may determine that the blood glucose level of the individual is consistently at an unhealthy level in the presence of certain people (e.g., friends or coworkers).

Similarly, if the diabetes management platform examines the cluster that includes the data series that are most similar to the target data series corresponding to the healthy glycemic state, then the diabetes management platform can discover characteristic(s) of "good" time intervals in which the blood glucose level is within the healthy range. For example, the diabetes management platform may determine that the blood glucose level of the individual is consistently at a healthy level on weekdays, following the performance of a certain activity (e.g., participating in a run or other athletic event), etc. As another example, the diabetes management platform may determine that the blood glucose level of the individual is consistently at a healthy level in the presence of certain people (e.g., family members).

Figure 9:
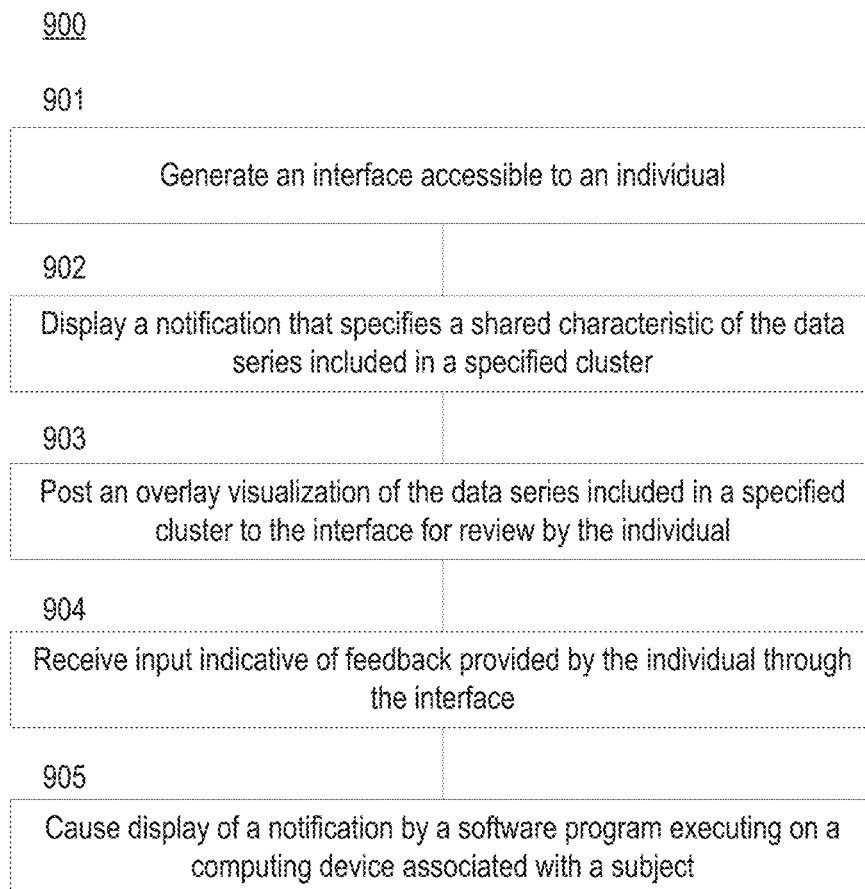
FIG. 9 depicts a flow diagram of a process for communicating the results of the process of FIG. 8 to an individual.

FIG. 9 depicts a flow diagram of a process 900 for communicating the results of process 800 to an individual. In some embodiments the individual is a person with diabetes, while in other embodiments the individual is interested in examining physiological data associated with some other person. Thus, the individual may be a health coach such as a medical professional (e.g., a physician or nurse), a diabetic health counselor, a family member, etc.

Initially, a computer program executing on a computing device will generate an interface accessible to an individual (step 901). The computer program can then display a visualization component corresponding to a specified cluster. For example, the computer program may display a notification that specifies a shared characteristic of the data series included in the specified cluster (step 902). As noted above, the shared characteristic may be associated with a "bad" time intervals in which the blood glucose level is not within the healthy range or "good" time intervals in which the blood glucose level is within the healthy range. Thus, the computer program may recommend that the individual seek the shared characteristic in the case of "good" time intervals or avoid the shared characteristic in the case of "bad" time intervals.

The computer program may also post an overlay visualization of the data series included in the specified cluster to the interface for review by the individual (step 903). The overlay visualization can take several different forms. For example, FIG. 7A depicts an example of a spaghetti plot that includes a different line for each evening over the course of several weeks. Because each cluster of data series is associated with a different color, the individual reviewing the chart to identify which data series are associated with consistently high/low blood glucose levels, whether those data series share any characteristics in common, etc. As another example, FIG. 7B depicts the rolling median and quartiles corresponding to each cluster.

In some embodiments, the computer program indicates on the interface that the visualization component and/or posted overlay visualization corresponds to the specified cluster. For example, the computer program may specify that the visualization component and/or posed overlay visualization are associated with weekday mornings, weekend evenings, etc. The computer program could specify such information in various manners. For example, in some embodiments the computer program posts a text caption identifying the specified cluster, while in other embodiments the computer program implements a color scheme that assigns a different color to each cluster, thereby ensuring the clusters are visually distinguishable from one another.

If the individual is a health coach responsible for monitoring the glycemic health of another person (also referred to as a "subject" or "patient"), then the computer program may receive input indicative of feedback provided through the interface (step 904). The feedback may include a recommendation for improving the subject's glycemic health. For example, the health coach may identify certain activities, foodstuffs, or time periods that are associated with a decline in the subject's glycemic health. In such embodiments, the computer program may cause display of a notification by another computer program executing on another computing device associated with the subject (step 905). For example, the computer program may communicate directly with the other computer program through a simple messaging technology. As another example, the computer program may transmit the notification to a diabetes management platform, which may be responsible for forwarding the notification to the other computer program.

The computer program may also enable the health coach to perform other action(s) involving the specified cluster. For example, the health coach may be able to make an annotation that is dynamically linked to the specified cluster. Generally, the annotation is subsequently presented to the subject for review. However, the annotation may not be shown to the subject (e.g., in instances where the health coach flags a time interval to be examined more closely in the future). As another example, the health coach may be able to generate a comparison of the specified cluster and at least one other cluster. These comparisons can permit the health coach to readily show the subject the variations in glycemic health across different clusters (e.g., mornings versus evenings).

Moreover, the computer program may enable the health coach to compile visualization component(s) using the multiple clusters, the specified clusters, etc. The visualization component(s) could include text, audio, video, or any combination thereof. Some visualization components only include text specifying a recommendation for improving glycemic health, while other visualization components include audio and/or video for incentivizing future performance of certain activities (e.g., compliance with a healthcare regimen may be incentivized by showing digital balloons, confetti, etc.). As another example, the computer program may identify trends in the clusters by examining changes in cluster count, cluster size, etc. Such trends may indicate whether the glycemic health of the subject is improving or declining over time.

Other steps may also be performed. For example, if the individual is the subject whose blood glucose level is being monitored, then the computer program may automatically display a recommendation for improving glycemic health. Thus, the recommendation may not be based on feedback provided by a health coach. Instead, the computer program could dynamically identify appropriate feedback based on the shared characteristic, distance measure, etc.

FIG. 10 depicts a flow diagram of a process 1000 for identifying similar data series in response to a selection of a specified data series. Execution of the process 1000 may enable a diabetes management platform to identify similar time intervals when an individual (e.g., a subject or a health coach) is already reviewing a trace from a specific time interval.

Steps 1001-1003 of FIG. 10 are substantially similar to steps 801 and 803-804 of FIG. 8. Thereafter, the diabetes management platform may store the similarity matrix in a database (step 1004). The database may be locally or remotely accessible. For example, in some embodiments the database is located on the computing device on which the diabetes management platform resides, while in other embodiments the database is located on a separate computing device than the diabetes management platform.

The diabetes management platform can receive input indicative of a selection of a first data series (step 1005). The individual may select the first data series by selecting an individual trace within a spaghetti plot as shown in FIG. 7A, by specifying one or more desired characteristics (e.g., using a filter function), etc. The diabetes management platform can then identify a second data series that is most similar to the first data series (step 1006). Such action may require that the diabetes management platform identify the data series whose distance measure with respect to the first data series indicates that it is the most similar data series to the first data series. In some embodiments, the diabetes management platform may identify multiple similar data series. Thus, the second data series may be one of a group of data series that are identified by the diabetes management platform as being similar to the first data series.

The diabetes management platform can also specify the second data series (as well as any other similar data series) on an interface for review by the individual (step 1007).

Unless contrary to physical possibility, it is envisioned that the steps described above may be performed in various sequences and combinations. For example, the diabetes management platform may simultaneously notify a subject whose blood glucose level is being monitored and a health coach responsible for monitoring the glycemic health of the subject. As another example, the diabetes management platform may periodically execute these processes such that updates on the glycemic health of the subject are provided on a periodic basis (e.g., daily, weekly, or monthly).

Other steps may also be included in some embodiments. For example, the diabetes management platform may perform an analytic process on the data series included in a specified cluster (or multiple clusters) to estimate the glycemic health state of the subject. Such action may be performed selectively. For instance, the diabetes management platform may only perform the analytic process responsive to discovering multiple clusters indicative of bad glycemic health, multiple clusters indicative of good glycemic health, a cluster having blood glucose values below a certain threshold, a cluster having blood glucose values above a certain threshold, etc. Examples of analytic processes include prioritizing recommendations provided for improving the glycemic state of the subject, examining glucose-related metrics critical in guiding diabetes treatment in a personalized manner, filtering certain data series and/or clusters from the data set examined by the diabetes management platform, etc.

Processing System

Figure 11:
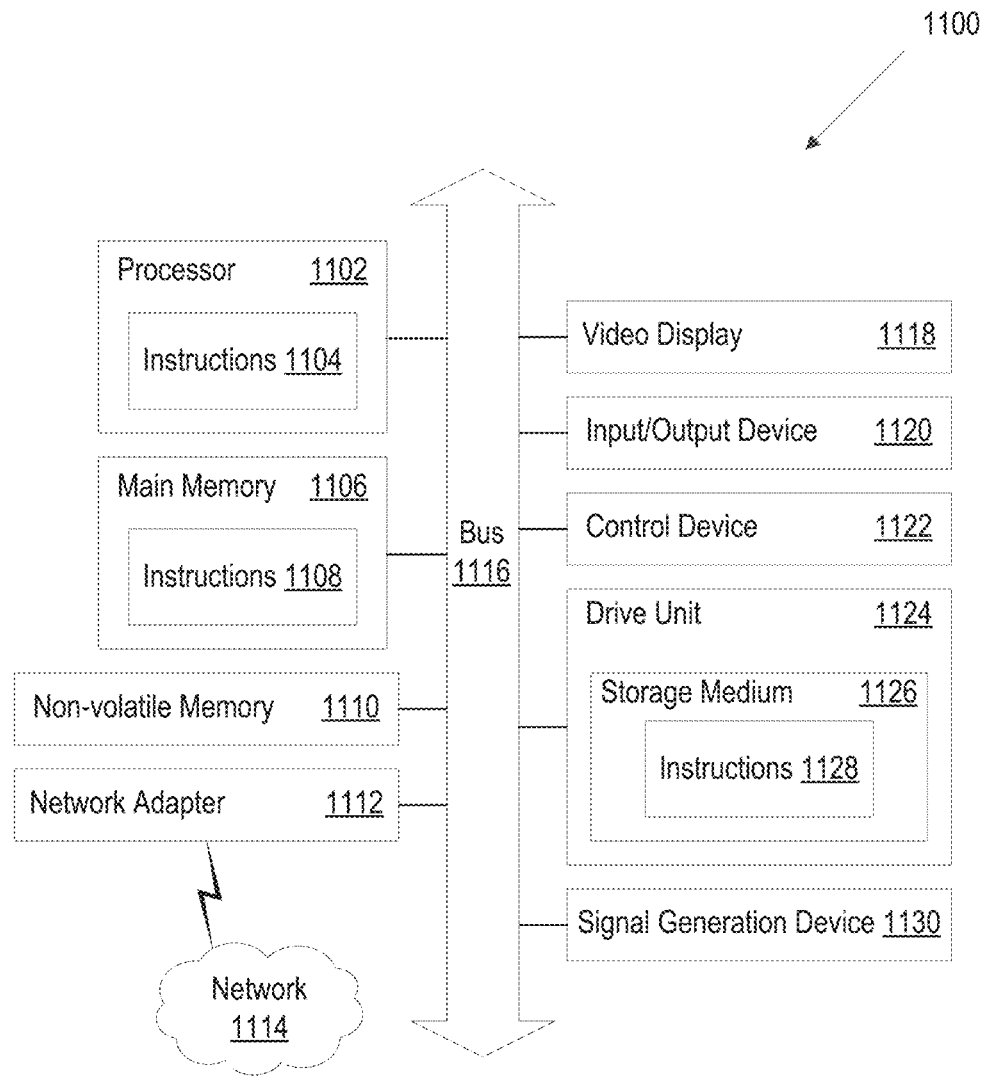
FIG. 11 is a block diagram illustrating an example of a processing system in which at least some operations described herein can be implemented.

FIG. 11 is a block diagram illustrating an example of a processing system 1100 in which at least some operations described herein can be implemented. For example, some components of the processing system 1100 may be hosted on a computing device that includes a diabetes management platform (e.g., diabetes management platform 202 of FIG. 2).

The processing system 1100 may include one or more central processing units ("processors") 1102, main memory 1106, non-volatile memory 1110, network adapter 1112 (e.g., network interface), video display 1118, input/output devices 1120, control device 1122 (e.g., keyboard and pointing devices), drive unit 1124 including a storage medium 1126, and signal generation device 1130 that are communicatively connected to a bus 1116. The bus 1116 is illustrated as an abstraction that represents one or more physical buses and/or point-to-point connections that are connected by appropriate bridges, adapters, or controllers. The bus 1116, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1100 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 1100.

While the main memory 1106, non-volatile memory 1110, and storage medium 1126 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1128. The term "machine-readable medium" and "storage medium" shall also be taken to include any medium that is capable of storing, encoding, or carrying a set of instructions for execution by the processing system 1100.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1104, 1108, 1128) set at various times in various memory and storage devices in a computing device. When read and executed by the one or more processors 1102, the instruction(s) cause the processing system 1100 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1110, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1112 enables the processing system 1100 to mediate data in a network 1114 with an entity that is external to the processing system 1100 through any communication protocol supported by the processing system 1100 and the external entity. The network adapter 1112 can include a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1112 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A computer-implemented method comprising:
    acquiring, by a processor, multiple data series that include
        (i) at least two data series comprised of measurements generated by a glucose monitoring device that monitors a time-varying blood glucose level of a subject, wherein each data series of the at least two data series corresponds to a different multi-hour interval of time over which the time-varying blood glucose level is periodically sampled at a frequency of at least two measurements per hour, and
        (ii) a target data series comprised of fabricated measurements that mimic a time-varying blood glucose level of an individual without diabetes;
    for each data series of the multiple data series,
        performing, by the processor, dynamic time warping to produce a distance measure for each other data series of the multiple data series,
            wherein the distance measure is indicative of similarity between a pair of data series;
    producing, by the processor, a similarity matrix from the distance measures associated with each data series of the multiple data series;
    sorting, by the processor, the multiple data series into multiple clusters based on the distance measures in the similarity matrix,
        wherein each cluster of the multiple clusters represents a grouping of data series covering a similar real-world behavior;
    identifying, by the processor, a particular cluster of the multiple clusters whose data series are least similar to the target data series based on the distance measures in the similarity matrix;
    calculating, by the processor, a median trace, a first quartile trace, and a third quartile trace for the particular cluster of the multiple clusters,
        wherein the first quartile trace corresponds to a midpoint between a smallest value and a median value over the corresponding time interval, and
        wherein the third quartile trace corresponds to a midpoint between a largest value and the median value over the corresponding time interval;
    posting, by the processor, a visualization of the particular cluster of the multiple clusters to a graphical user interface for review by a health coach, wherein the posted visualization includes the median trace, the first quartile trace, and the third quartile trace;

indicating, by the processor, on the graphical user interface that the posted visualization corresponds to the particular cluster; and enabling, by the processor, the health coach to make an annotation through the graphical user interface that is dynamically linked to the particular cluster.

2. The computer-implemented method of claim 1, wherein said sorting comprises:

applying a clustering algorithm to the similarity matrix, wherein the clustering algorithm is configured to:

determine a count of how many clusters in the multiple clusters, determine respective cluster size represented by a count of data series included in each cluster, and assign each data series of the multiple data series to a cluster of the multiple clusters.

3. The computer-implemented method of claim 2, further comprising:

enabling, by the processor, the health coach to compile one or more visualization components using the multiple clusters; and identifying, by the processor, a trend in the multiple clusters by examining changes in cluster count, cluster size, or any combination thereof over time.

4. The computer-implemented method of claim 1, further comprising:

receiving, by the processor, input indicative of feedback to the subject provided by the health coach through the graphical user interface;

compiling, by the processor, a visualization component based on the feedback; and causing, by the processor, display of the visualization component by a computer program executing on a computing device associated with the subject.

5. The computer-implemented method of claim 1, wherein each multi-hour interval of time corresponds to a same time period relatively within each day across multiple days.

6. The computer-implemented method of claim 1, further comprising:

identifying, by the processor, an outlier data series based on the distance measures included in the similarity matrix, wherein each distance measure associated with the outlier data series exceeds a specified threshold;

filtering, by the processor, the outlier data series from the multiple data series; and forming, by the processor, the multiple clusters based on the distance measures included in the similarity matrix, wherein said filtering causes the outlier data series to not be considered when forming the multiple clusters.

7. The computer-implemented method of claim 1, wherein each multi-hour interval of time is associated with, and corresponds to, a natural rhythm or cycle, and wherein the natural rhythm or cycle is a circadian cycle, a menstrual cycle, a feeding cycle, an elimination cycle, or any combination thereof.

8. The computer-implemented method of claim 1, further comprising:

performing, by the processor, an analytic process on one or more data series included in the particular cluster of the multiple clusters to determine a glycemic health state of the subject.

9. A non-transitory computer-readable medium with instructions stored thereon that, when executed by a processor, cause the processor to perform operations comprising:

acquiring multiple data series that include (i) at least two data series comprised of measurements generated by a glucose monitoring device that monitors a blood glucose level of a subject, wherein each data series of the at least two data series corresponds to a different multi-hour interval of time over which the blood glucose level is periodically sampled at a frequency of at least two measurements per hour, and (ii) a target data series comprised of fabricated measurements that mimic a blood glucose level of an individual without diabetes;

for each data series of the multiple data series, applying a similarity algorithm to produce a distance measure for each other data series of the multiple data series, wherein the distance measure is indicative of similarity between a pair of data series;

automatically sorting the multiple data series into one or more clusters based on the distance measures associated with the multiple data series in response to said applying;

identifying a specified cluster whose one or more data series are least similar to the target data series based on the distance measures produced by the similarity algorithm;

detecting a shared characteristic of the one or more data series;

causing display of a visualization component on an interface generated by a computer program executing on an electronic device associated with an individual, wherein the visualization component specifies the shared characteristic of the one or more data series; and enabling the individual to create an annotation through the interface that is linked to the one or more data series.

10. The non-transitory computer-readable medium of claim 9, wherein the interface is configured to facilitate interactions between the subject and a health coach responsible for monitoring glycemic health of the subject.

11. The non-transitory computer-readable medium of claim 10, wherein the operations further comprise:

receiving input indicative of feedback provided by the health coach through the computer program executing on the electronic device; and causing display of a second visualization component on a second interface generated by a second computer program executing on a second electronic device associated with the subject, wherein content of the second visualization component is based on the feedback provided by the health coach.

12. The non-transitory computer-readable medium of claim 9, wherein the interface is configured to serve as an informative dashboard for the subject.

13. The non-transitory computer-readable medium of claim 9, wherein the shared characteristic is either reflected in the one or more data series or derivable from the one or more data series or metadata provided with the one or more data series.

14. The non-transitory computer-readable medium of claim 9, wherein each multi-hour interval of time is between 3 and 12 hours in length to match a feeding cycle, and wherein the at least two data series correspond to a same time period across multiple days.

15. The non-transitory computer-readable medium of claim 9, wherein each multi-hour interval of time interval is 24 hours in length to match a circadian cycle, and wherein the at least two data series correspond to consecutive days.

16. The non-transitory computer-readable medium of claim 9, wherein said applying comprises:
performing dynamic time warping by non-linearly warping the pair of data series in a time dimension,
wherein said performing produces the distance measure that is independent of non-linear variations in the time dimension, the distance measure accounting for similar events taking place at different times.

17. The non-transitory computer-readable medium of claim 9, wherein the visualization component specifies a recommendation for improving glycemic health of the subject, and wherein the recommendation is based on the shared characteristic of the one or more data series.

18. A method comprising:
acquiring at least two data series comprised of measurements generated by a glucose monitoring device associated with a subject,
wherein each data series of the at least two data series corresponds to a different multi-hour interval of time over which a blood glucose level of the subject is periodically sampled at a frequency of at least two measurements per hour;
acquiring a target data series comprised of fabricated measurements that mimic a time-varying blood glucose level of an individual without diabetes;
for each data series of the at least two data series,
performing dynamic time warping to produce a distance measure for the target data series and each other data series of the at least two data series,
wherein each distance measure is independent of non-linear variations in a time dimension between a pair of data series;
producing a similarity matrix from the distance measures associated with each data series of the at least two data series;
sorting the at least two data series into multiple clusters by applying a spectral clustering algorithm to the distance measures in the similarity matrix,
wherein each cluster of the multiple clusters represents a grouping of data series covering a similar real-world behavior;
identifying a particular cluster of the multiple cluster whose data series are least similar to the target data series based on the distance measures in the similarity matrix; and
outputting, in response to said identifying, information indicative of the particular cluster for display on a digital interface.

* * * * *